United States Patent
Condie et al.

(10) Patent No.: US 7,031,772 B2
(45) Date of Patent: Apr. 18, 2006

(54) METHOD AND APPARATUS FOR RATE RESPONSIVE ADJUSTMENTS IN AN IMPLANTABLE MEDICAL DEVICE

(75) Inventors: Catherine R. Condie, Shoreview, MN (US); John D. Wahlstrand, Shoreview, MN (US); Gerald A. Portzline, Fridley, MN (US); Yong Kyun Cho, Maple Grove, MN (US); John S. Brandstetter, Coon Rapids, MN (US); Luc R. Mongeon, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 597 days.

(21) Appl. No.: 10/134,560

(22) Filed: Apr. 29, 2002

(65) Prior Publication Data

US 2003/0204211 A1    Oct. 30, 2003

(51) Int. Cl.
*A61N 1/365* (2006.01)
(52) U.S. Cl. .......................................... 607/20; 607/18
(58) Field of Classification Search ............ 607/18–20
See application file for complete search history.

(56) References Cited

U.S. PATENT DOCUMENTS

| | | | |
|---|---|---|---|
| 4,867,162 A | 9/1989 | Schaldach | |
| 5,065,759 A | 11/1991 | Begemann et al. | |
| 5,423,869 A * | 6/1995 | Poore et al. | 607/18 |
| 5,562,711 A * | 10/1996 | Yerich et al. | 607/17 |
| 6,246,901 B1 | 6/2001 | Benaron | |

FOREIGN PATENT DOCUMENTS

| | | |
|---|---|---|
| DE | 195/20836 A1 | 10/1995 |
| WO | WO 00/24457 | 5/2000 |

* cited by examiner

*Primary Examiner*—George R. Evanisko
(74) *Attorney, Agent, or Firm*—Michael C. Soldner; Girma Wolde-Michael (57) ABSTRACT

A method and an apparatus for performing rate responsive control in an implantable medical device using a scaling factor. Sensor data is acquired using a sensor operatively coupled with the implantable medical device. At least one setpoint for controlling a rate of therapy is generated, the setpoint being based upon the sensor data. A scaling factor adjustment process is performed for scaling the internal sensor data to correlate the sensor data to the setpoint. The rate of therapy is adjusted based upon the scaling factor adjustment.

20 Claims, 8 Drawing Sheets

METHOD AND APPARATUS FOR RATE RESPONSIVE ADJUSTMENTS IN AN IMPLANTABLE MEDICAL DEVICE

BACKGROUND OF THE INVENTION

This invention relates generally to the control of implantable medical devices, and, more particularly, the present invention relates to a method and apparatus for performing rate responsive adjustments in an implantable medical device.

DESCRIPTION OF THE RELATED ART

The technology explosion in the implantable medical device industry has resulted in many new and innovative devices and methods for analyzing and improving the health of a patient. The class of implantable medical devices now includes pacemakers, implantable cardioverters, defibrillators, neural stimulators, and drug administering devices, among others. Today's state-of-the-art implantable medical devices are vastly more sophisticated and complex than earlier ones, capable of performing significantly more complex tasks. The therapeutic benefits of such devices have been well proven.

There are many implementations of implantable medical devices that provide data acquisition of important physiological data from a human body. Many implantable medical devices are used for cardiac monitoring and therapy. Often these devices include sensors that are placed in blood vessels and/or chambers of the heart. Often these devices are operatively coupled with implantable monitors and therapy delivery devices. For example, such cardiac systems include implantable heart monitors and therapy delivery devices, such as pacemakers, cardioverters, defibrillators, heart pumps, cardiomyostimulators, ischemia treatment devices, drug delivery devices, and other heart therapy devices. Most of these cardiac systems include electrodes for sensing and gain amplifiers for recording and/or driving sense event signals from the inter-cardiac or remote electrogram (EGM).

As the functional sophistication and complexity of implantable medical device systems have increased over the years, it has become increasingly useful to include a system for facilitating communication between one implantable medical device and another implantable medical device or external device, for example, a programming console, monitoring system, or the like. Shortly after the introduction of the earliest pacemakers, it became apparent that it would be desirable for physicians to non-invasively obtain information regarding the operational status of the implantable medical device, and/or to exercise at least some control over the device, e.g., to turn the device on or off or adjust the pacing rate, after implant. As new, more advanced features have been incorporated into implantable medical devices, it has been increasingly useful to convey correspondingly more information to and/or from the device relating to the selection and control of those features.

Generally, a number of physiological data such as ventricular pressure, oxygen supply in the patient's blood, EGM data, a patient's breathing patterns, and the like, are collected and used by the implantable medical devices implanted into a human body. The data can then be used to analyze the condition of a patient's physical state. Many times, information gathered by the implantable medical device may provide indications of certain conditions in a patient's body. The information gathered by the implantable medical devices may be used to validate and/or test new algorithms and/or firmware implemented into the implantable medical devices. However, information gathered by the implantable medical devices used to validate new algorithms and/or operations of the implantable medical devices may be limited and/or insufficient.

Many times, delivery of therapy is based upon one or more physiological responses detected by an implantable medical device. Often, based upon a person's activity, state of mind, etc., physiological responses in a patient's body may vary. Certain physiological responses detected by the implantable medical device can be used to provide appropriate therapy to the patient in order to maintain proper operation of the implantable medical device and the heart.

A ventilation physiological response that relates to the breathing and/or volume of air intake in a patient's body may be used to affect delivery of therapy to influence proper operation of a patient's heart. However, these physiological signals may cause an over-response to particular activities performed by a patient. For example, a small activity may drive the rate at which certain therapy is delivered at a rate that is too high. Many times, certain physiological data may be used to create a therapy delivery signal that may take a step function, which may cause a dramatic increase in the rate of therapy delivered to a patient's heart. This could detrimentally influence the state of the patient's health. Many times a step function may cause overreaction by the implantable medical device, which may cause damage to a person's health.

The present invention is directed to overcoming, or at least reducing the effects of, one or more of the problems set forth above.

SUMMARY OF THE INVENTION

In one aspect of the present invention, a method is provided for performing rate responsive control in an implantable medical device using a scaling factor. Internal sensor data is acquired using an internal sensor operatively coupled with the implantable medical device. At least one setpoint for controlling a rate of therapy is generated, the setpoint being based upon the internal sensor data. A scaling factor adjustment process is performed for scaling the internal sensor data to correlate the internal sensor data to the setpoint. The rate of therapy is adjusted based upon the scaling factor adjustment.

In another aspect of the present invention, an apparatus is provided for performing rate responsive control in an implantable medical device using a scaling factor. The apparatus of the present invention includes a processor; a control logic unit operatively coupled to the processor, the control logic unit generating at least one control signal in response to a command from the processor; a data acquisition controller operatively coupled with the control logic unit, the data acquisition controller acquiring internal data in response to an assertion of at least one control signal from the control logic unit; a memory unit operatively coupled with the data acquisition controller, the memory unit storing the acquired internal data; and a firmware unit operatively coupled with at least one of the processor, the control logic unit, and the memory unit, the firmware unit calculating an activities of daily living (ADL) setpoint and performing a scaling factor adjustment process for scaling the internal data to correlate the internal sensor data to the ADL setpoint.

BRIEF DESCRIPTION OF THE DRAWINGS

The inventions may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving the operation of implantable medical devices (e.g., pacemakers, cardio defibrillators, the like). The operation of an implantable medical device include collecting, storing, and analyzing physiological data relating to a patient, and/or delivering therapy (e.g., cardiac therapy) to a portion of a patient's body. Often, these tasks are performed by an implantable medical system, which includes an implantable medical device. Based upon the analysis performed by the implantable medical system, one or more therapies may be delivered to a particular portion of a patient's body. One example of such a therapy is a cardiac therapy, which is delivered to a patient's heart. Interpretation of the physiological data and/or data relating to unusual activities in the patient's body is important in determining the behavior (e.g., therapy deliver patterns, etc.) of the implantable medical device.

Often, delivery of therapy by the implantable medical device is performed based on physiological sensor data. Certain rates of therapy delivery may be influenced by physiological data, such as a minute ventilation (MV), which may drive or influence therapy to a patient's heart. However, an under-response to activity performed by a patient may occur as a result of driving therapy rates based upon physiological data, such as minute ventilation. Embodiments of the present invention provide for implementing a scaling factor to adjust a physiological signal, such as minute ventilation, in order to control/influence the delivery of therapy in response to particular activities performed by a patient.

Generally, a signal that provides a guideline for normal delivery of therapy, such as an activities of daily living boundary (ADL), is used to drive the therapy delivery performed by the implantable medical device. The activities of daily living boundary may provide an average rate of therapy delivery for a particular patient. Generally, the minute ventilation that is responsive to certain activities performed by the patient may drive the therapy delivery rate above the activities of daily living boundary. Embodiments of the present invention provide for applying a scaling factor in order to reduce the possibility of a step increase in the rate of therapy delivery that may occur as a result of an increase in the minute ventilation signal.

Figure 1:
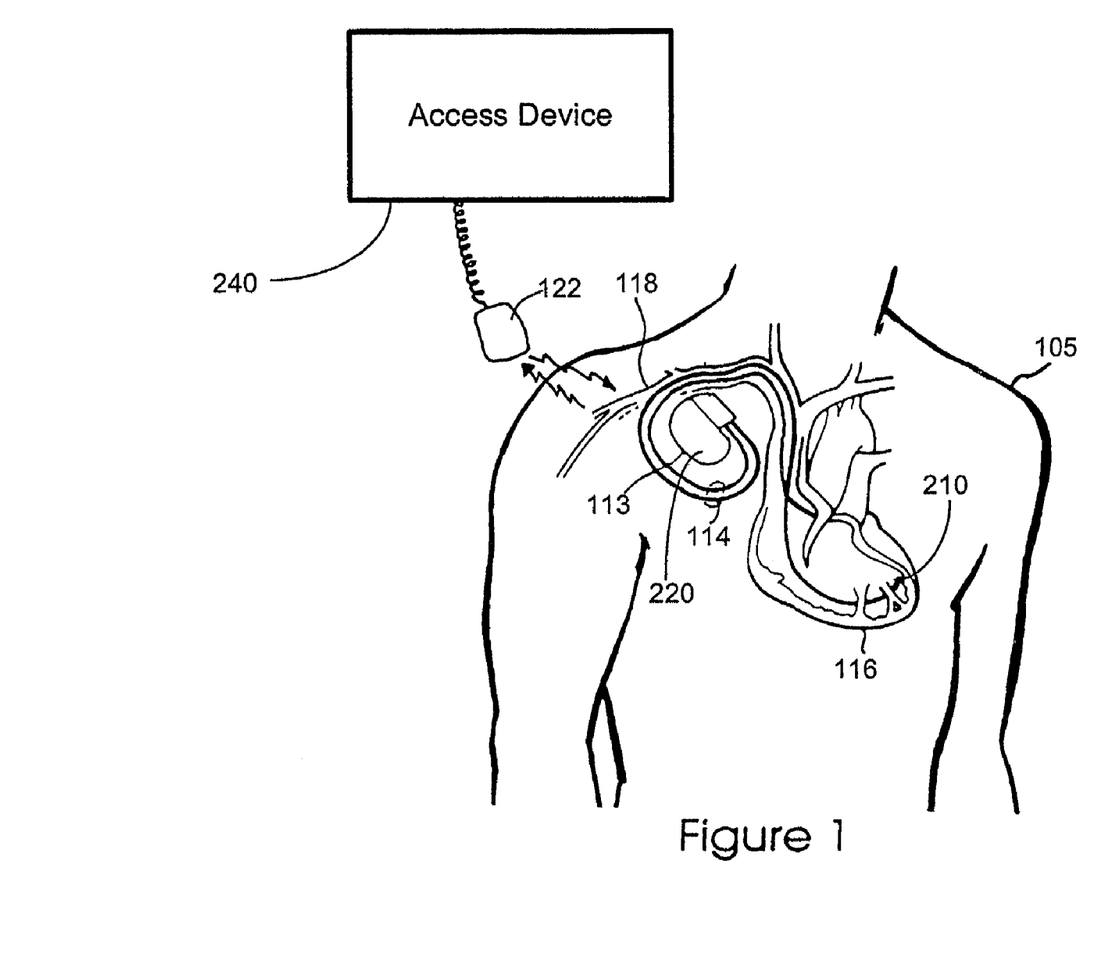
FIG. 1 is a simplified diagram of an implementation of an implantable medical device, in accordance with one illustrative embodiment of the present invention.

Turning now to FIG. 1, one embodiment of implementing an implantable medical device into a human body is illustrated. A sensor/therapy delivery device 210 (e.g., devices attached to leads 114) placed within the heart of the human body 105 is used to acquire and process physiological data. An implantable medical device 220 collects and processes a plurality of data acquired from the human body 105. In one embodiment, the implantable medical device 220 may be a pacemaker or a defibrillator. The data acquired by the implantable medical device 220 can be monitored by an external system, such as the access device 240, comprising a programming head 122, which remotely communicates with the implantable medical device 220. The programming head 122 is utilized in accordance with medical device programming systems known to those skilled in the art having the benefit of the present disclosure for facilitating two-way communication between the implantable medical device 220 and the access device 240.

In one embodiment, a plurality of access devices 240 can be employed to collect a plurality of data processed by the implantable medical device 220 in accordance with embodiments of the present invention. The implantable medical device 220 is housed within a hermetically sealed, biologically inert outer canister or housing 113, which may itself be conductive so as to serve as an electrode in the implantable medical device 220 pacing/sensing circuit. One or more implantable medical device 220 sensors/leads, collectively identified with reference numeral 114 in FIG. 1, are electrically coupled to the implantable medical device 220 and extend into the patient's heart 116 via a vein 118. Disposed generally near a distal end of the leads 114 are one or more exposed conductive electrodes (sensor/therapy delivery device 210) for receiving electrical cardiac signals or delivering electrical pacing stimuli to the heart 116. The leads 114 may be implanted with their distal end situated in either the atrium or ventricle of the heart 116. In an alternative embodiment, the sensor/therapy delivery device 210, or the leads 114 associated with the sensor/therapy delivery device 210, may be situated in a blood vessel on the heart 116, such as a vein 118.

In one embodiment, the implantable medical device 220 illustrated in FIG. 1 is capable of performing a rate-responsive treatment based on physiological and/or non-physiological data detected by the implantable medical device 220. One method of performing a rate responsive therapy delivery is to determine a target rate based upon predetermined programming for the operation of the implantable medical device 220 and new physiological data and other data sensed from the patient's body 105. The data sensed from the patient's body 105 may include data from sensors that detect a patient's 105 activity, body movements (accelerations experienced by the patient), oxygen levels in the patient's 105 blood, EGC readings, and the like). The rate responsive pacing rate (or target pacing rate TPR) may be defined by Equation 1 as:

$$TPR = \text{Predetermined Pacing Rate} + f(\text{Sensor Data}) \quad \text{Equation 1}$$

wherein f(Sensor Data) is typically a linear or monotonic function of the sensor data.

One method of performing a rate responsive therapy delivery is by calculating the patient's minute ventilation. Minute ventilation has been demonstrated clinically to be a parameter that correlates directly to the actual metabolic and physiologic needs of the patient 105. Minute ventilation (MV) may be defined by Equation 2 as:

$$MV = \text{Respiration Rate} \times \text{Tidal Volume} \quad \text{Equation 2}$$

wherein the respiration rate is represented by breaths per minute taken by the patient 105 and the tidal volume is represented in volume in liters (e.g., volume of air intake into the lungs on the patient 105).

In one embodiment, the implantable medical device 220 measures changes in the transthoracic impedance, which is generally proportional to minute ventilation. Since minute ventilation is a function of the respiration rate and the tidal volume (see Equation 2), the minute ventilation may be a physiological indicator of changes in the metabolic demands in a patient's body 105, which may provide an indication of an adjustment to therapy delivery rate provided by the implantable medical device 220. One exemplary method of performing a rate responsive therapy delivery may be found in U.S. Pat. No. 5,562,711, "Method and Apparatus For Rate-Responsive Cardiac Pacing."

Figure 2:
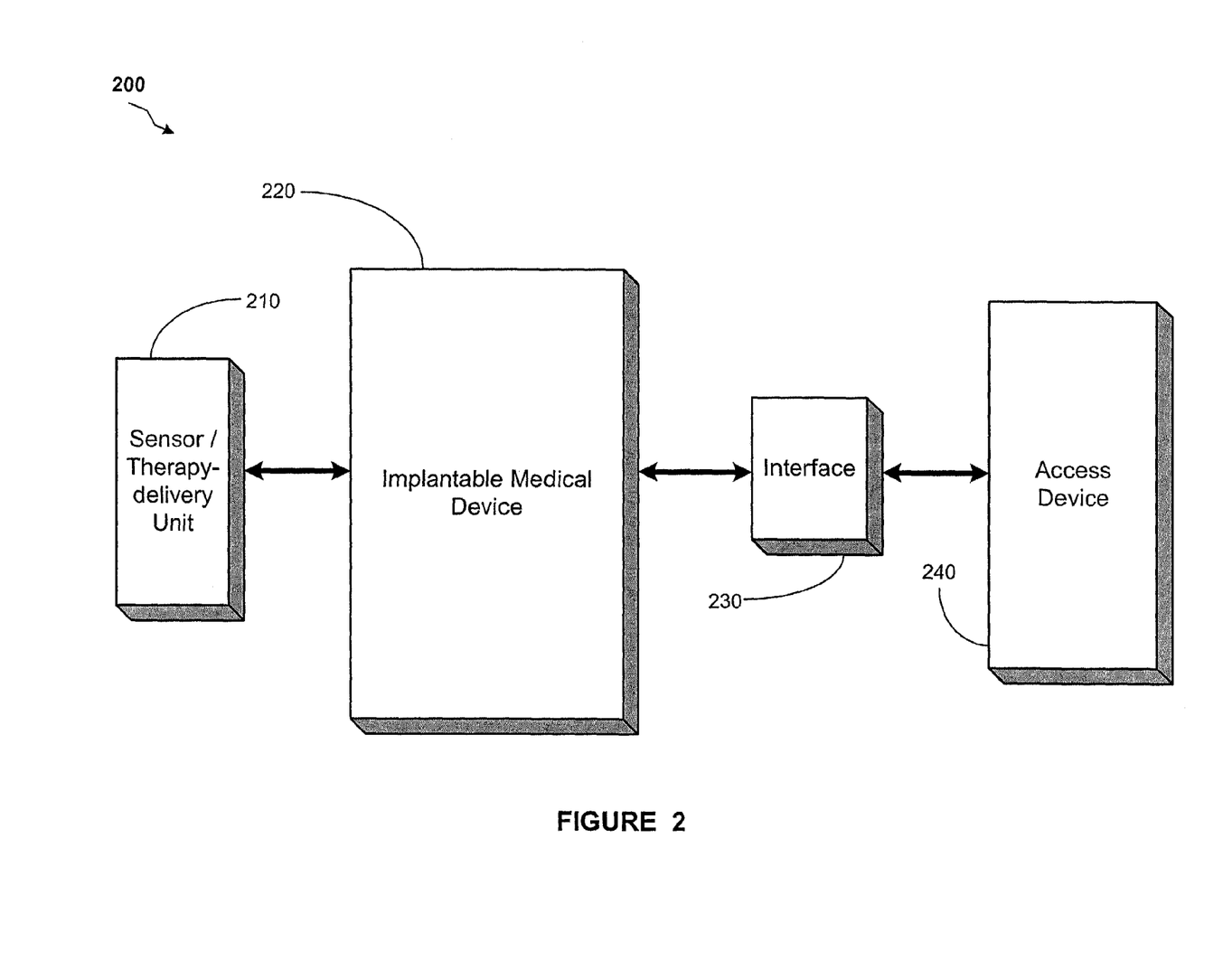
FIG. 2 is a simplified block diagram representation of an implantable medical system in accordance with one illustrative embodiment of the present invention.

Turning now to FIG. 2, a system 200, in accordance with an embodiment of the present invention, is illustrated. The system 200 includes a sensor/therapy delivery unit 210, an implantable medical device 220, and an access device 240. Embodiments of the present invention provide a plurality of physiological data and non-physiological data from the sensor/therapy delivery unit 210 to the implantable medical device 220, which are then processed and stored in the implantable medical device 220. The sensor/therapy delivery unit 210 may include a plurality of sensors that are capable of acquiring physiological and non-physiological data. Based upon data from the sensor(s) and other factors, the implantable medical device 220 may deliver a therapy to a portion of the patient's body 105, via the sensor/therapy delivery unit 210. The access device 240 can be used to reprogram and/or make modifications to the operation of the implantable medical device 220.

Figure 3:
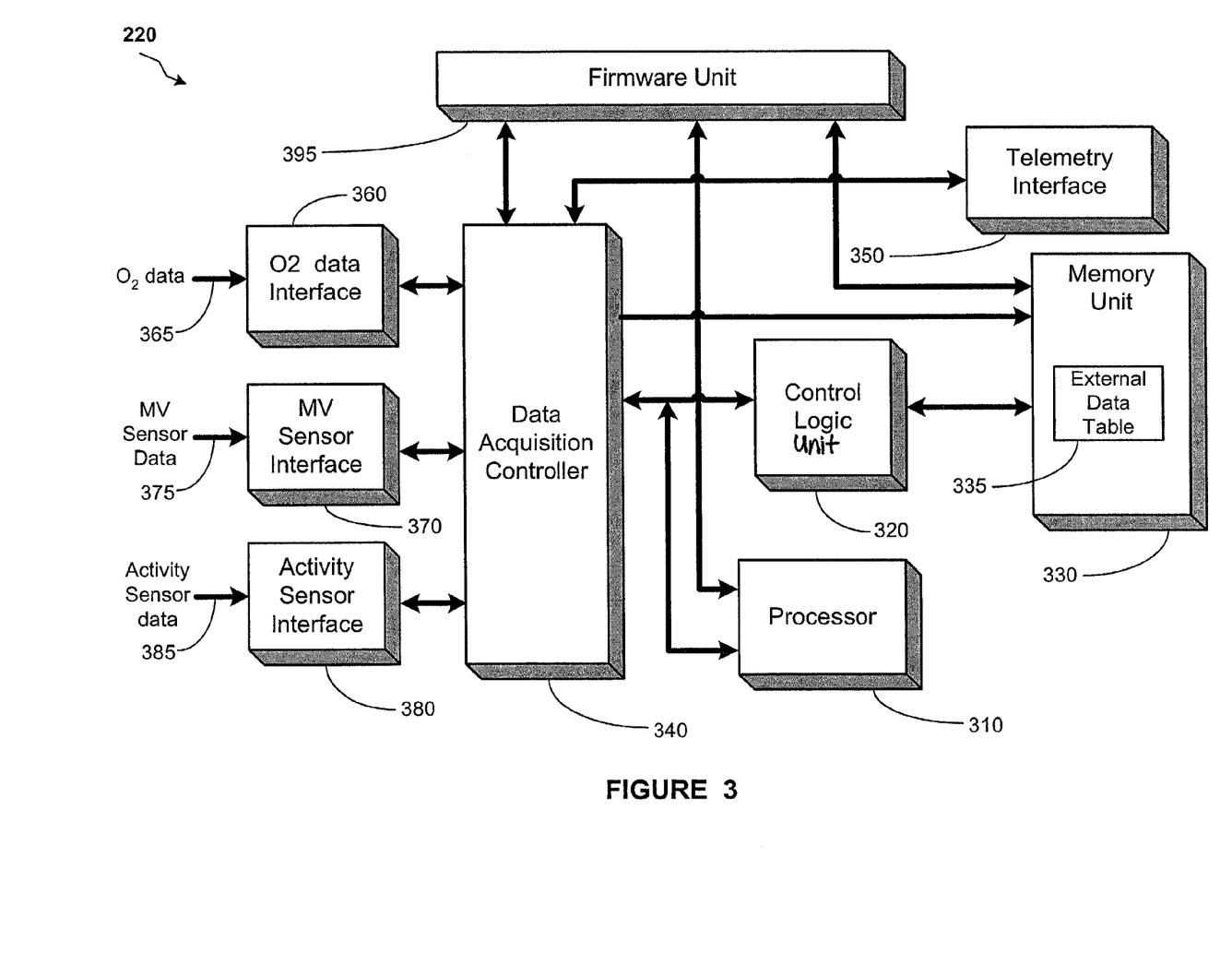
FIG. 3 is a more detailed block diagram representation of the implantable medical device of FIGS. 1 and 2, in accordance with one embodiment of the present invention.

Turning now to FIG. 3, a more detailed block diagram depiction of one embodiment of the implantable medical device 220 is illustrated. The implantable medical device 220 includes a processor 310, a control logic unit 320, a memory unit 330, a data acquisition controller 340, a telemetry interface 350, an $O_2$ data interface 360, a minute ventilation (MV) sensor interface 370, and an activity sensor interface 380. In one embodiment, sensor interfaces 360, 370, 380 may be operatively coupled to the data acquisition controller 340. Processor 310 controls the operation of the implantable medical device 220 and utilizes the control logic unit 320 to perform a plurality of operations, including memory access and storage operations. Processor 310 communicates with the control logic unit 320 and the data acquisition controller 340 via a bus line. The control logic 320 sends control signals to the memory unit 330 for controlling and installing memory, and to the data acquisition controller 340, which controls the acquisition of physiological data and drives output signals to the telemetry interface 350.

In one embodiment, the telemetry interface 350 is capable of facilitating real-time access of physiological data acquired by the data acquisition controller 340. Therefore, a physician can view physiological data on a real-time basis by accessing the data acquisition controller 340 via the telemetry interface 350. The telemetry interface 350 can be used to download modifications to the firmware that is used to operate the implantable medical device 220. The data acquisition controller 340 can prompt the data interfaces 360, 370, 380 to retrieve physiological data, such as $O_2$ data 365, MV sensor data 375, and activity sensor data 385, process such physiological data 365, 375, 385, and deliver physiological data 365, 375, 385 to the data acquisition controller 340. The data interfaces 360, 370, 380 can perform a number of analog-to-digital conversions and time-interval conversions, known to those skilled in the art, upon the acquired physiological data 365, 375, 385. The data interfaces 360, 370, 380 can acquire, condition, and process physiological data 365, 375, 385 and forward said data to the data acquisition controller 340.

The MV sensor interface 370 is capable of receiving data from a minute ventilation sensor. The MV sensor interface 370, in one embodiment, may condition the accelerometer data received from an accelerometer and forward the conditioned data to the data acquisition controller 340. Furthermore, the activity sensor interface 380 receives activity sensor data 385 from an activity sensor, which in one embodiment may be a piezoelectric device or an accelerometer, and conditions such activity sensor data 385 and forwards the conditioned activity sensor data 385 to the data acquisition controller 340.

As illustrated in FIG. 3, the implantable medical device 220 further includes a firmware unit 395. The firmware unit 395, in one embodiment, includes a plurality of sets of program/descriptive-language circuitry/logic circuitry that may be programmed. Sections of the firmware unit 395 can provide controllability of the operations of the implantable medical device 220. In one embodiment, the firmware unit 395, in conjunction with the processor 310, controls the operation of the implantable medical device 220.

The memory unit 330 includes an external data table 335 capable of storing sensor data acquired from an external source (external sensor data). External sensor data can be downloaded into the memory unit 330 and into the external data table 335, via the access device 240. In an alternative embodiment, external sensor data, or external data, can be downloaded into the external data table 335 via the telemetry interface 350. In one embodiment, real-time external data sensor capture may be placed into the memory unit 330 via the telemetry interface 350.

Figure 4:
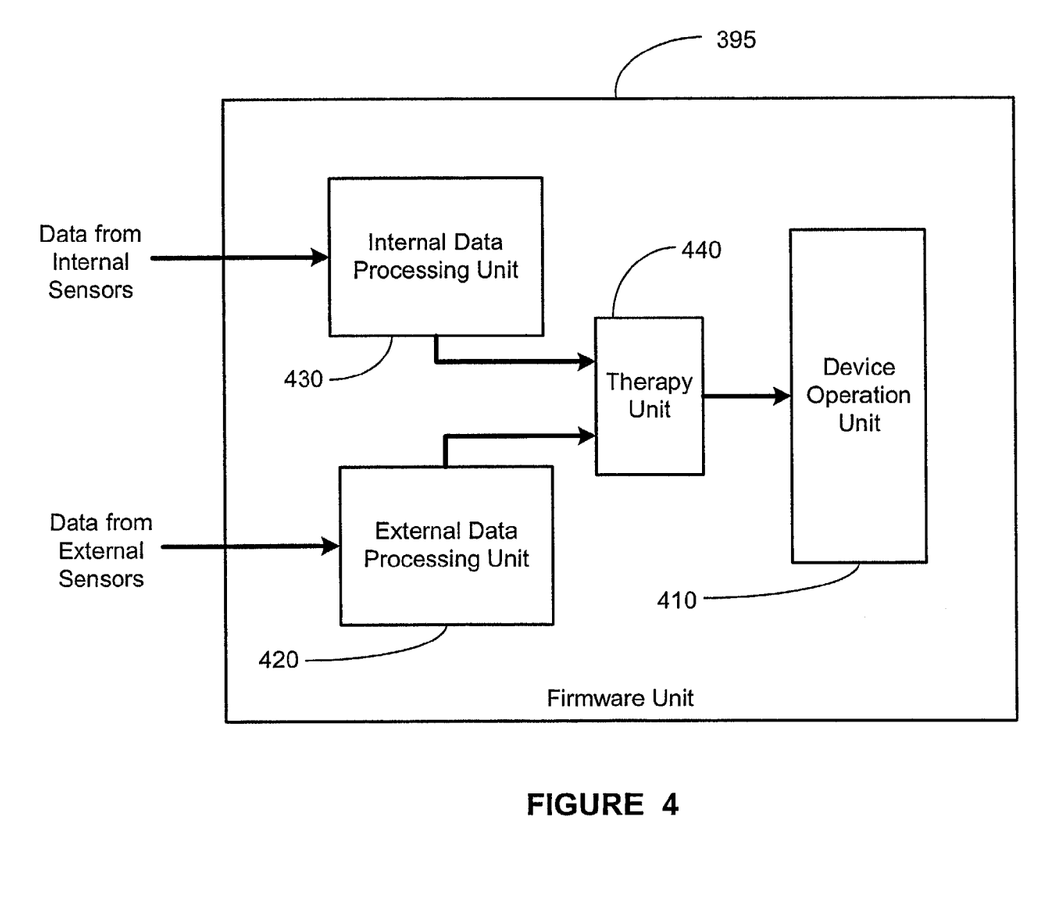
FIG. 4 is a more detailed block diagram representation of the firmware unit of FIG. 3, in accordance with one embodiment of the present invention.

Turning now to FIG. 4, a simplified block-diagram representation of one embodiment of the firmware unit 395, is illustrated. In one embodiment, the firmware unit 395 includes a device operation unit 410, an external data processing unit 420, an internal data processing unit 430, and a therapy unit 440. Data from internal sensors (i.e., sensors placed inside the patient's body 105 and operatively coupled with the implantable medical device 220) such as an MV (minute ventilation) sensor, an R2 data sensor, and/or an activity sensor (a pezio-electronic ceramic device) is acquired by the internal data processing unit 430 for processing. Further, data from an external sensor (e.g. an accelerometer attached onto a patient's body 105) is acquired by the external data processing unit 420.

In one embodiment, the external data processing unit 420 receives stored external sensor data from the external data table 335 in the memory unit 330. Utilizing the external data processing unit 420, external data can be transmitted to the implantable medical device 220, along with the internal sensor data, which are both sent to the therapy unit 440. The therapy unit 440 processes the external sensor data and the internal sensor data to determine a therapy delivery schedule. In one embodiment, the therapy unit 440 is capable of performing a rate responsive therapy delivery based upon the internal sensor data and the external sensor data.

The device operation unit 410 includes software, firmware, and/or hardware that provide logic for performing a plurality of operations as employed by the implantable medical device 220. For example, the therapy delivery schedule determined by the therapy unit 440 is used by the device operation unit 410 to prompt the implantable medical device 220 to deliver therapies based upon the data from the therapy unit 440.

Figure 5:
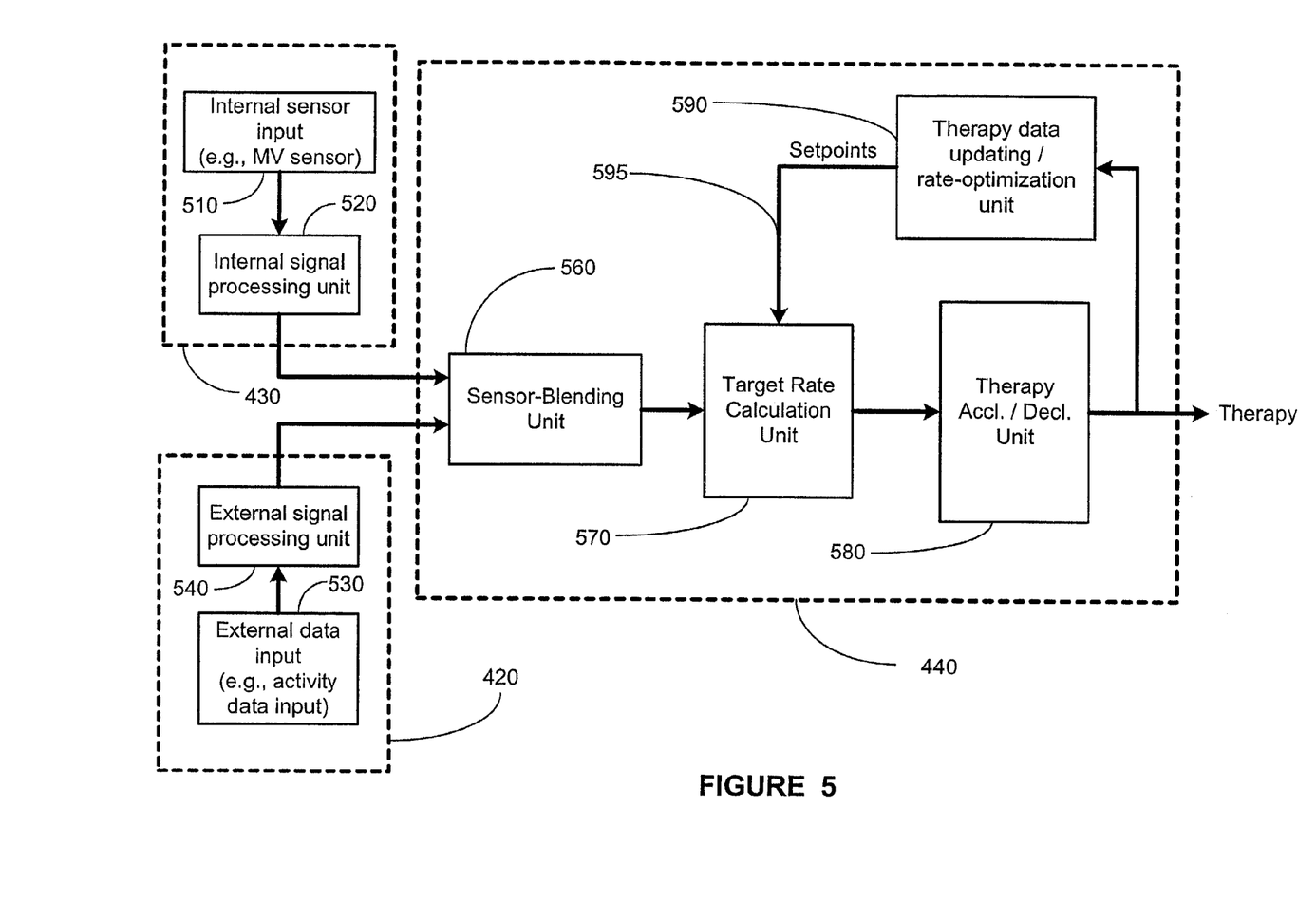
FIG. 5 is a more detailed block diagram representation of the therapy unit of FIG. 4, and its surrounding structures, in accordance with one embodiment of the present invention.

Turning now to FIG. 5, a more detailed block-diagram depiction of the interaction between the external data processing unit 420, the internal data processing unit 430, and the therapy unit 440, is illustrated. In one embodiment, the internal data processing unit 430 includes an internal sensor input 510 and an internal signal processing unit 520. The internal signal processing unit 520 processes the internal sensor input 510. The internal sensor input 510 may be internal sensor data, such as MV sensor data 375. Similarly, the external data processing unit 420 may send external sensor data to the therapy unit 440. The external data processing unit 420 includes an external signal processing unit 540, which processes the external data input 530. The external data input 530 may include sensor data from an external device such as an accelerometer or an activity sensor.

In one embodiment, the therapy unit 440 includes the sensor-blending unit 560, a target rate calculation unit 570, a therapy accelerator/decelerator unit 580, and a therapy data updating/rate-optimization unit 590. The sensor-blending unit 560 acquires the processed internal sensor data from the internal signal processing unit 520 and the processed external sensor data from the external signal processing unit 540 and combines the data. In one embodiment, the sensor-blending unit 560 blends the MV sensor data 375 with corresponding accelerometer data (external sensor data).

The data from the sensor-blending unit 560 is sent to the target rate calculation unit 570 for determining a target pacing rate of the therapy to be delivered based upon the input received (blending of the MV sensor data 375 and the accelerometer data). Therefore, physiological and non-physiological changes experienced by the patient 105 will drive a change in the therapy rate to accommodate for particular activities, such as exercise for example. The target rate calculation unit 570 uses a setpoint rate of therapy delivery, and modifies the setpoint rate based upon data from the sensor-blending unit 560. Based upon the target pacing rate calculations, the therapy accelerator/decelerator unit 580 reduces or increases the therapy rate.

The therapy delivered by the implantable medical device 220 may be based upon the reduced or increased therapy rate as determined by the therapy accelerator/decelerator unit 580. Furthermore, this therapy rate is fed back to the therapy data updating/rate-optimization unit 590. The therapy data updating/rate-optimization unit 590 updates histogram bins that store the histograms relating to the operation of the implantable medical device 220. Furthermore, a rate profile optimization is performed by the therapy data updating/rate-optimization unit 590 to optimize the therapy rate based upon longer-term data from the patient's body 105 (e.g., performed once a day). The therapy data updating/rate-optimization unit 590 provides a setpoint therapy target pacing rate to the target rate calculation unit 570 via a line 595, completing the feedback loop illustrated in FIG. 5. Therefore, therapy delivered to the patient 105 is monitored and adjusted depending on the activities and/or the physiological needs of the patient 105.

Figure 6:
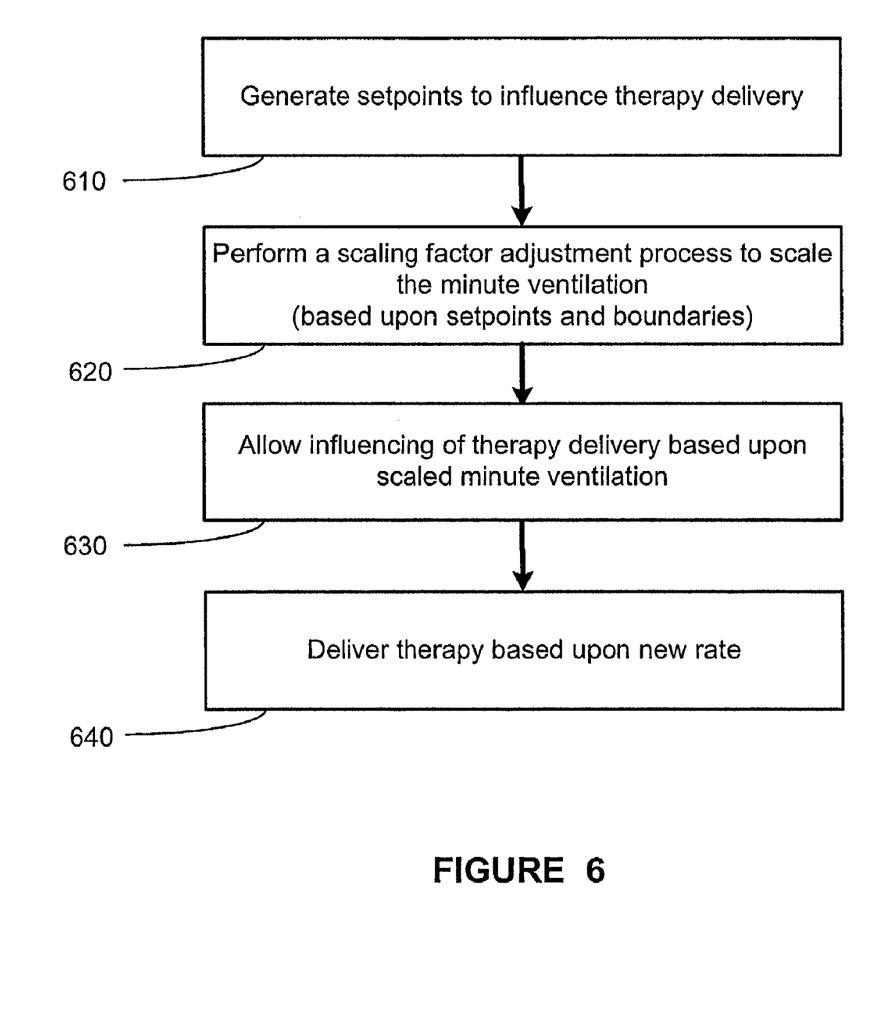
FIG. 6 is a flowchart depiction of a method, in accordance with one illustrative embodiment of the present invention.

Turning now to FIG. 6, a flow chart depiction of the method in accordance with one embodiment of the present invention is illustrated. In general, the implantable medical device 220 generates setpoints in order to influence the delivery of therapy (e.g., the rate of therapy delivery). These setpoints, such as an ADL setpoint, are used to generate a target rate for delivery of therapy (block 610). The setpoints are generated based upon the particular physiological characteristics of a patient 105. The ADL setpoint is generated based upon-the therapy rates believed to be optimum for the daily average pacing/stimulation requirements for a patient's 105 heart 116.

Figure 7:
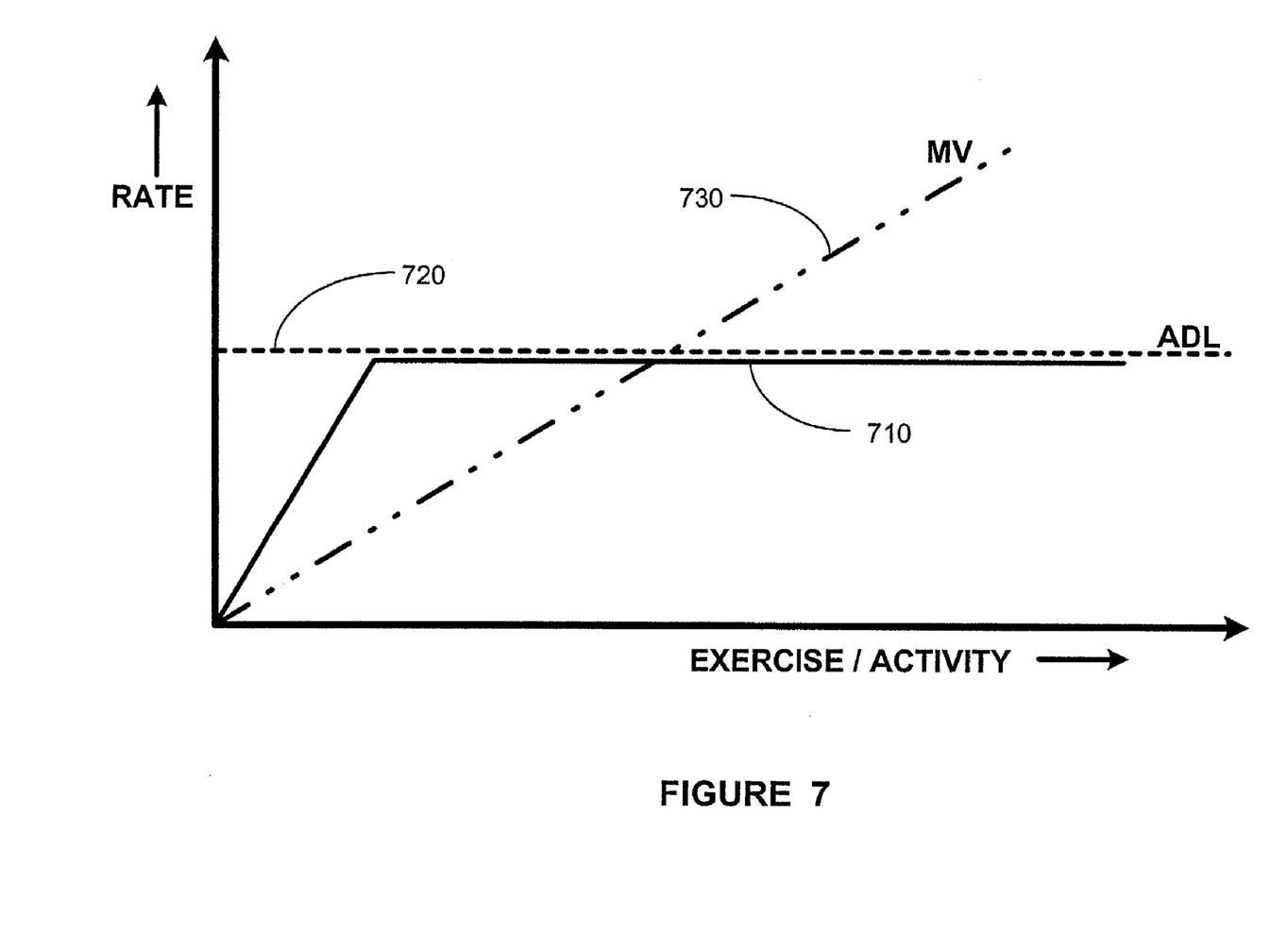
FIG. 7 is a graph displaying an increase in a therapy delivery rate based upon an increase in the exercise/activity performed by a patient.

The implantable medical device 220 performs a scaling factor adjustment process to scale the minute ventilation based upon the setpoints and boundaries of therapy delivery rates that may be established (block 620). The scaling factor may be used to scale the minute ventilation variations such that the response from an accelerometer (not shown) may be matched to the variability of the minute ventilation sensor response. Upon adjustment/scaling of the minute ventilation, influencing of the therapy delivery is performed based on the scaled minute ventilation (block 630). As shown in the graph illustrated in FIG. 7, the rate of therapy delivery (designated by a curve 710) is generally set by the ADL (designated by a curve 720). In order to reduce the possibility of a step function increase in the rate (curve 710), the minute ventilation, which results in a more controlled increase of the rate as the rate rises above the ADL boundary (see curve 730) is scaled. The influence of the scaled MV (see curve 730), which is scaled by the scaling factor, is adjusted such that the rate is less likely to experience a step-function rise in response to an increase in an exercise/activity performed by a patient 105.

Utilizing the scaled minute ventilation reduces the likelihood of an over-reaction by the implantable medical device 220 in response to any activities performed by the patient 105. Therefore, a slight increase in activity performed by the patient 105, such as short-term exercise, would be less likely to cause a step-function rise in the rate of delivery of therapy. Turning back to FIG. 6, after utilizing the scaled MV, therapy is delivered based on the newly calculated rate (block 640). A more detailed description of the steps illustrated in FIG. 6, is provided in FIG. 8 and the accompanying description below.

Figure 8:
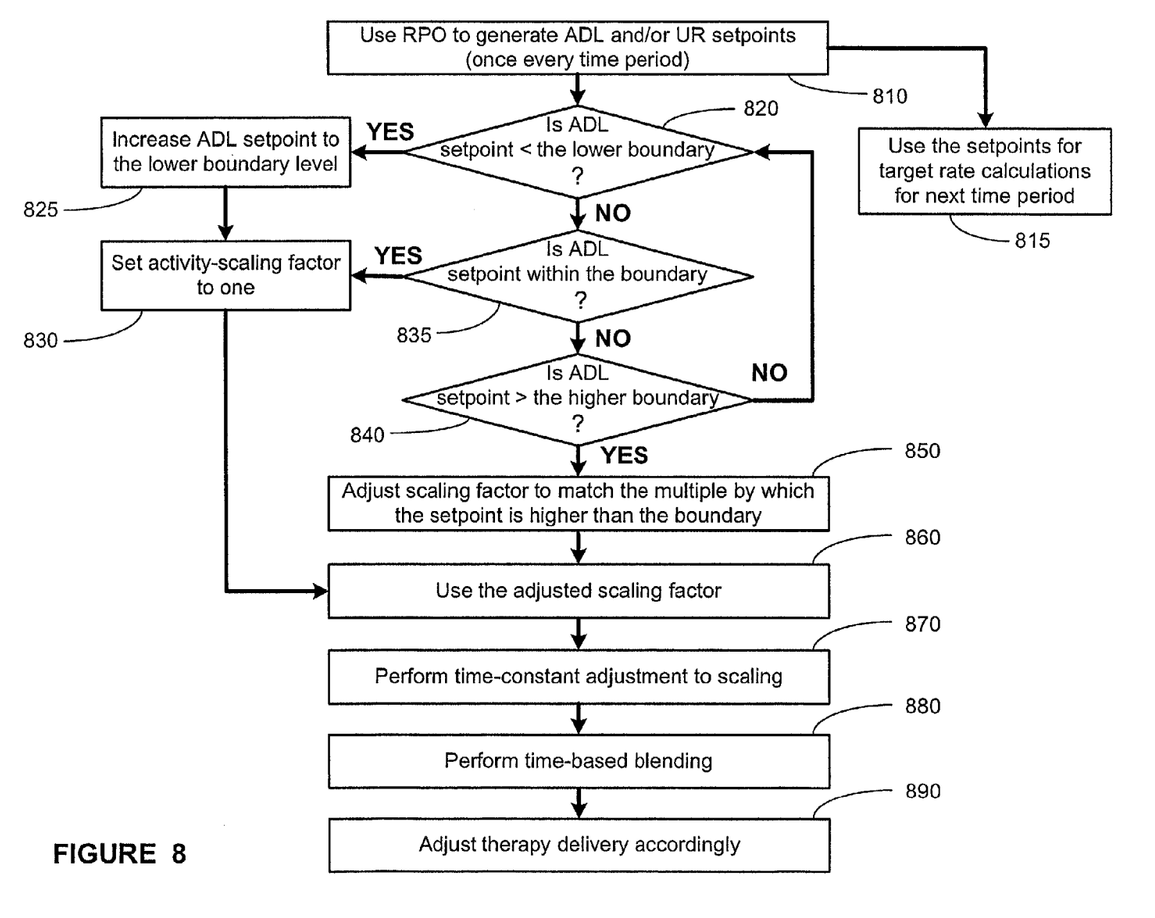
FIG. 8 is a more detailed flowchart depiction of the methods taught by the present invention, in accordance with one illustrative embodiment of the present invention.

Turning now to FIG. 8, a more detailed flow chart depiction of the method provided in FIG. 6 is illustrated. The implantable medical device 220 implements a rate profile optimization calculation process in order to generate an optimized rate profile data for a particular patient 105. The rate profile optimization calculation process takes into account many factors, such as the patient's 105 general health, weight, age, exercise habits, and the like. The implantable medical device 220 uses the rate profile optimization (RPO) calculation process in order to generate ADL and upper rate (UR) setpoints, usually at a frequency of once per specified time period (block 810). In one embodiment, the RPO may be based upon results from the MV sensor. Furthermore, the specified rate period, in one embodiment, may be once per day.

In one embodiment, once per day, the rate profile optimized calculation is used to generate ADL and UR setpoints that are used in the target rate calculation for the next day. In one embodiment, RPO calculations may be based on a single sensor, hence, the RPO calculations may be based on the internal sensor input 510 (e.g., MV sensor input). The activity-scaling factor is generally calculated to optimize the scaling to match the internal sensor input 510 (e.g., MV sensor input). This better enables the implantable medical device 220 to perform adjustments to the external data input 530 (e.g., an accelerometer data output), which generally provides a fairly predictable response, in order to match the response from the internal sensor input 510 (e.g., MV sensor input), which is generally more variable.

The calculated ADL and UR setpoints are used for the target rate calculations for the subsequent time period (block 815). For example, the ADL/UR setpoints calculated today, may be used for the target rate calculations for tomorrow. The implantable medical device 220 determines whether the ADL setpoint is less than the specified lower boundary of acceptable therapy rates (block 820). When a determination is made that the sensor counts are less than the boundary, the implantable medical device 220 increases the ADL setpoint in order to approximately match the sensor counts to the lower boundary (block 825).

Once the ADL setpoint is increased in order to approximately match the boundary level, the activity-scaling factor is set to one (block 830). In other words, when the ADL setpoint is increased within the boundary level, no scaling is required, therefore, a scaling factor of one is applied. Once the scaling factor is set to one, it is then used by the implantable medical device 220 to influence the rate of therapy delivery, which is described in more detail below. When the implantable medical device 220 determines that the ADL setpoint is not less than the lower boundary, a determination is made whether the ADL setpoint is within the lower and upper boundary (block 835). When the implantable medical device 220 determines that the ADL setpoint is within the upper and lower boundaries, the device sets the activity scaling factor to one, as shown in the path from block 835 to block 830. Subsequently, the scaling factor of one is utilized to generate the therapy rate (see path from block 835 to 830 to 860).

When the implantable medical device 220 determines that the ADL setpoint is not within the boundaries, a determination is made whether the ADL setpoint is greater than the upper boundary (block 840). When the implantable medical device 220 determines that the ADL setpoint is greater than the upper boundary, the implantable medical device 220 adjusts the scaling factor to match the multiple or factor by which the ADL setpoint is higher than the boundary (block 850). In other words, when the ADL setpoint, which may be based on the internal sensor input 510 (e.g., MV sensor input), is greater than the upper boundary, multiples/factors of the upper boundary are checked. This multiplier/factor is then used as the activity scaling factor (block 860). For example, if the ADL setpoint is greater than twice the upper boundary, but less than three times the upper boundary, the implantable medical device 220 sets the activity scaling factor to two and the ADL setpoint is left unchanged.

Once the steps described in either block 830 or in block 850 are used to adjust the activity scaling factor, the implantable medical device 220 utilizes the activity scaling factor to influence the delivery of therapy (block 860). In one embodiment, the implantable medical device 220 performs a time-constant adjustment to the scaling factor (block 870). In one embodiment, the methods for linear interpolation of ADL setpoint values described above may not take into consideration the time constants of the measurements. In order to consider the time constants in interpolating ADL values, the average heart rate excursion (e.g., exercise bout) may be tracked for rates in regions where the internal and external sensor inputs 510, 530 are blended (e.g., blended by the sensor-blending unit 560). In one embodiment, the linear interpolation of the ADL setpoints may be adjusted to compensate/account for shorter average heart rate excursions (e.g., shorter exercise bouts).

Subsequently, the implantable medical device 220, in one embodiment, may perform a time-based blending function to determine the rate of the delivery of therapy (block 880). In some cases, algorithms used to blend the internal and external sensor inputs 510, 530 may be based on the previous sensor rate. This may cause errors in the time constants relating to the measurements described above. In order to reduce this error, a more appropriate use of the internal and external sensor inputs 510, 530 would be to use the internal and external sensors 510, 530 to cause the activity of the patient 105 to drive therapy rates over the full range of the heart rate excursion, but generally at the onset of exercise. For example, the internal sensor input 510 (e.g., the MV sensor input) may be blended by the sensor-blending unit 560 based upon the amount of time the patient 105 was exercising. In other words, the blending performed by the sensor-blending unit 560 may be based on the rate of change of the MV in a short term average (STA), such as a 32 second short term average. This would take into consideration individual differences in the physiologic time constant for minute ventilation.

Additionally, an RPO time freeze and/or an RPO stability freeze may be calculated in order to improve calculations of the ADL setpoints. Many times the RPO may become stabilized for a particular patient 105 after a few months of adaptation. However, as an additional precaution, the implantable medical device 220 may freeze the RPO after a period of time (e.g., 3 months). In an alternative embodiment, as part of a more complex form, the implantable medical device 220 may slow the adaptation time constant to limit the ability of the algorithm to adapt and modify the RPO, unless the cause for adaptation was present for a substantially longer period of time (e.g., months rather than weeks).

Based upon the adjustments described above, the implantable medical device 220 adjusts the rate of therapy delivery accordingly (block 890). The implantable medical device 220 then delivers the therapy at the adjusted rate. Utilizing the scaling function described by embodiments of the present invention, a more appropriate reaction to the delivery of therapy can be performed based upon physiological changes in a patient's body 105. Therefore, the possibility of over-reaction by the implantable medical device 220 based upon a change in activity by a patient 105 are reduced by implementing the teachings provided by embodiments of the present invention.

The above detailed description is an illustrative example of an embodiment in accordance with the present invention, of the implementation of the implantable medical device 220 described above. It should be appreciated that other implementations and/or embodiments can be employed within the spirit of the present invention. The teachings of the present invention can be utilized for a variety of systems relating to electrical circuitry, including circuitry that utilize stored charge.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is set forth in the claims below.

What is claimed:

1. A method for performing rate responsive control in an implantable medical device, comprising:
   acquiring an internal sensor data using an internal sensor operatively coupled with said implantable medical device;
   generating at least one setpoint for controlling a rate of therapy, said setpoint based upon said internal sensor data;
   performing a scaling factor adjustment process for scaling said internal sensor data to correlate said internal sensor data to said setpoint; and
   adjusting said rate of therapy based upon said scaling factor adjustment, wherein performing said scaling factor adjustment process further comprises:
   performing a rate profile optimization (RPO) process to determine a rate profile;
   generating an activities of daily living (ADL) setpoint based upon said RPO;
   increasing said ADL setpoint based upon a determination that said ADL setpoint is below a lower boundary of an acceptable therapy rate;
   setting an activity scaling factor to one in response to at least one of increasing said ADL setpoint and a determination that said ADL setpoint is within said lower boundary and an upper boundary of an acceptable therapy rate;
   calculating a multiplier of said ADL setpoint, in response to a determination that said ADL setpoint is above said upper boundary, said multiplier being egual to a factor by which said ADL setpoint is above said upper boundary; and
   adjusting said scaling factor to match said multiplier.

2. The method described in claim 1, wherein acquiring said internal sensor data using said internal sensor further comprises acquiring minute ventilation (MV) data.

3. The method described in claim 1, wherein generating said setpoint for controlling said rate of therapy further comprises generating an activities of daily living (ADL) setpoint based upon an average daily rate.

4. The method described in claim 3, wherein generating said setpoint based upon an activities of daily living setpoint further comprises:
   blending said internal data with an external data;
   calculating a target pacing rate for a delivery of therapy based at least partially upon at least one of said blending of said internal and extemal data and an initial setpoint therapy target pacing rate;
   modifying a therapy delivery rate based upon said target pacing rate; and
   calculating a new setpoint therapy target pacing rate as feed back for calculating a subsequent target pacing rate.

5. The method described in claim 4, wherein blending said internal data with an external data further comprises blending said internal data with activity data.

6. The method described in claim 1, wherein performing said scaling factor adjustment process for scaling said internal sensor input to correlate said internal sensor data to said setpoint further comprises performing a scaling factor adjustment upon a minute ventilation (MV) data.

7. The method described in claim 1, wherein performing said rate profile optimization process to determine a rate profile further comprises determining a rate for therapy delivery based upon at least one physiological profile of a patient.

8. The method described in claim 1, wherein generating an activities of daily living (ADL) setpoint based upon said RPO further comprises calculating an average therapy rate appropriate for a patient based upon at least one physiological profile of said patient.

9. The method described in claim 1, further comprising performing a time constant adjustment to said scaling factor, said time constant adjustment comprising calculating a time constant relating to interpolating an ADL setpoint value by tracking an average heart excursion.

10. A method for performing rate responsive control in an implantable medical device, comprising:
    acquiring minute ventilation data using an internal sensor operatively coupled with said implantable medical device;
    generating at least one activities of daily living (ADL) setpoint for controlling a rate of therapy, said ADL setpoint based upon said minute ventilation;
    performing a scaling factor adjustment process for scaling said minute ventilation data to correlate said internal sensor data to said setpoint; and
    adjusting said rate of therapy based upon said scaling factor adjustment, wherein performing said scaling factor adjustment process further comprises:
    performing a rate profile optimization (RPO) process to determine a rate profile;
    generating an activities of daily living (ADL) setpoint based upon said RPO;
    increasing said ADL setpoint based upon a determination that said ADL setpoint is below a lower boundary of an acceptable therapy rate;
    setting an activity scaling factor to one in response to at least one of increasing said ADL setpoint and a determination that said ADL setpoint is within said lower boundary and an upper boundary of an acceptable therapy rate;
    calculating a multiplier of said ADL setpoint in response to a determination that said ADL set point is above said upper boundary, said multiplier being equal to a factor by which said ADL setpoint is above said upper boundary; and
    adjusting said scaling factor to match said multiplier.

11. An apparatus for performing rate responsive control in an implantable medical device, comprising:

means for acquiring an internal sensor data using an internal sensor operatively coupled with said implantable medical device;

means for generating at least one setpoint for controlling a rate of therapy, said setpoint based upon said internal sensor data;

means for performing a scaling factor adjustment process for scaling said internal sensor data to correlate said internal sensor data to said setpoint; and means for adjusting said rate of therapy based upon said scaling factor adjustment, wherein the means for performing said scaling factor adjustment process further comprises:

performing a rate profile optimization (RPO) process to determine a rate profile;

generating an activities of daily living (ADL) setpoint based upon said RPO;

increasing said ADL setpoint based upon a determination that said ADL setpoint is below a lower boundary of an acceptable therapy rate;

setting an activity scaling factor to one in response to at least one of increasing said ADL setpoint and a determination that said ADL setpoint is within said lower boundary and an upper boundary of an acceptable therapy rate;

calculating a multiplier of said ADL setpoint, in response to a determination that said ADL setpoint is above said upper boundary, said multiplier being equal to a factor by which said ADL setpoint is above said upper boundary; and adjusting said scaling factor to match said multiplier.

12. A computer readable medium having computer-executable instructions for performing a method, comprising:

acquiring an internal sensor data using an internal sensor operatively coupled with said implantable medical device;

generating at least one setpoint for controlling a rate of therapy, said setpoint based upon said internal sensor data;

performing a scaling factor adjustment process for scaling said internal sensor data to correlate said internal sensor data to said setpoint; and adjusting said rate of therapy based upon said scaling factor adjustment, wherein performing a scaling factor adjustment process further comprises:

performing a rate profile optimization (RPO) process to determine a rate profile;

generating an activities of daily living (ADL) setpoint based upon said RPO;

increasing said ADL setpoint based upon a determination that said ADL setpoint is below a lower boundary of an acceptable therapy rate;

setting an activity scaling factor to one in response to at least one of increasing said ADL setpoint and a determination that said ADL setpoint is within said lower boundary and an upper boundary of an acceptable therapy rate;

calculating a multiplier of said ADL setpoint, in response to a determination that said ADL setpoint is above said upper boundary, said multiplier being equal to a factor by which said ADL setpoint is above said upper boundary; and adjusting said scaling factor to match said multiplier.

13. The computer readable medium described in claim 12, wherein acquiring said internal sensor data using said internal sensor further comprises acquiring minute ventilation (MV) data.

14. The computer readable medium described in claim 12, wherein generating said setpoint for controlling said rate of therapy further comprises generating an activities of daily living (ADL) setpoint based upon an average daily rate.

15. The computer readable medium described in claim 12, wherein generating said setpoint based upon an activities of daily living setpoint further comprises:

blending said internal data with an external data;

calculating a target pacing rate for a delivery of therapy based at least partially upon at least one of said blending of said internal and external data and an initial setpoint therapy target pacing rate;

modifying a therapy delivery rate based upon said target pacing rate; and calculating a new setpoint therapy target pacing rate as feedback for calculating a subsequent target pacing rate.

16. The computer readable medium described in claim 15, wherein blending said internal data with an external data further comprises blending said internal data with activity data.

17. The computer readable medium described in claim 12, wherein performing said scaling factor adjustment process for scaling said internal sensor input to correlate said internal sensor data to said setpoint further comprises performing a scaling factor adjustment upon a minute ventilation, (MV) data.

18. The computer readable medium described in claim 12, wherein performing said rate profile optimization process to determine a rate profile further comprises determining a rate for therapy delivery based upon at least one physiological profile of a patient.

19. The computer readable medium described in claim 12, wherein generating an activities of daily living (ADL) setpoint based upon said RPO further comprises calculating an average therapy rate appropriate for patient based upon at least one physiological profile of said patient.

20. The computer readable medium described in claim 12, the method further comprising performing a time constant adjustment to said scaling factor, said time constant adjustment comprising calculating a time constant relating to interpolating an ADL setpoint value by tracking an average heart excursion.

* * * * *